(12) United States Patent
Artús Surroca et al.

(10) Patent No.: US 6,448,404 B1
(45) Date of Patent: Sep. 10, 2002

(54) CRYSTALLINE FORM OF NEFAZODONE AND PROCESS FOR THE PREPARATION THEREOF

(75) Inventors: Juan J. Artús Surroca, Vilanova i la Geltrú; LlorençRafecas Jané, Llorenç del Penedés; Montserrat Jané Bonet, Vilanova i la Geltrú, all of (ES)

(73) Assignee: Finaf 92, S.A., Barcelona (ES)

( * ) Notice: Subject to any disclaimer, the term of this patent is extended or adjusted under 35 U.S.C. 154(b) by 0 days.

(21) Appl. No.: 09/418,760

(22) Filed: Oct. 15, 1999

(30) Foreign Application Priority Data

Oct. 23, 1998 (ES) ................................................ 9802223

(51) Int. Cl.$^7$ ............................................ C07D 403/06
(52) U.S. Cl. ................... 544/366; 514/254.05
(58) Field of Search .......................................... 544/366

(56) References Cited

U.S. PATENT DOCUMENTS

| | | | |
|---|---|---|---|
| 4,338,317 A | 7/1982 | Temple, Jr. et al. | ........ 514/252 |
| 4,487,773 A | 12/1984 | Temple, Jr. et al. | ........ 514/252 |
| 5,256,664 A | * 10/1993 | Mayol et al. | ................ 514/252 |
| 5,886,004 A | * 3/1999 | Audia et al. | ................ 514/280 |

* cited by examiner

*Primary Examiner*—Emily Bernhardt
(74) *Attorney, Agent, or Firm*—Scully, Scott, Murphy & Presser

(57) ABSTRACT

A crystalline form of nefazodone and a process for the preparation thereof are disclosed. The crystalline form, or crystalline nefazodone hydrochloride dihydrate, has the chemical name of 2-[3-[4-(3-chlorophenyl)-1-piperazinyl] propyl]-5-ethyl-2,4-dihydro-4-(2-phenoxyethyl)-3H-1,2,4-triazol-3-one hydrochloride dihydrate and formula

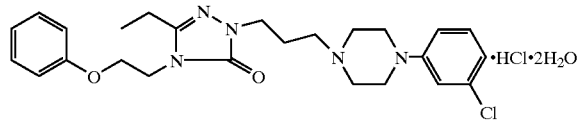

The process comprises preparing the crystalline nefazodone hydrochloride dihydrate by crystallising nefazodone hydrochloride dihydrate from an organic solvent/water mixture comprising at least 0.2 parts by volume of an organic solvent for each part by volume of water.

29 Claims, 8 Drawing Sheets

CRYSTALLINE FORM OF NEFAZODONE AND PROCESS FOR THE PREPARATION THEREOF

DESCRIPTION

1. Field of the Invention

The present invention relates to a crystalline form of nefazodone and to a process for the preparation thereof.

More particularly, the invention relates to the crystalline nefazodone hydrochloride dihydrate, having the chemical name of 2-[3-[4-(3-chlorophenyl)-1-piperazinyl]propyl]-5-ethyl-2,4-dihydro-4-(2-phenoxyethyl)-3H-1,2,4-triazol-3-one hydrochloride dihydrate, of formula

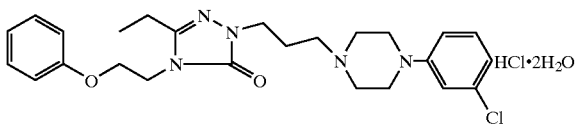

and to a process for the preparation thereof.

Nefazodone is a well-known therapeutic agent having an antidepressant activity. For therapeutical purposes, it is preferably used in the hydrochloride form. Two forms of this compound are known: Polymorph A (m.p. 186–187° C.) and Polymorph B (m.p. 181–182° C.) and the former is the preferred product in the pharmaceutical field.

2. Prior Art

The purification of nefazodone still presents a number of difficulties.

U.S. Pat. No. 4,338,317 describes the preparation of nefazodone and a process for purifying same. To be precise, Example 2 (col. 9, lines 17–47, describes the purification of the free base by acidification in ethanol with ethanolic hydrogen chloride and crystallisation to provide a hydrated form (0.25 mole water) of nefazodone hydrochloride, melting at 175–177°C. The description continues to say that a non-hydrated sample obtained according to that process also melted at 175–177° C.

Example 6 of U.S. Pat. No. 4,487,773 describes a method of purifying crude nefazodone hydrochloride in methylene chloride, with filtration and concentration of the filtrate at reduced pressure. Crystallisation of the residue from isopropanol affords a still crude product (yield 62.5%) which is further crystallised from water and then from isopropanol to afford nefazodone hydrochloride melting at 180–182.5° C.

Gary D. Madding (J. Het. Chem., 22, 1121, 1985) describes an even more time-consuming method of purification. In fact, the method described on page 1125, left hand column, lines 38–51, comprises a first purification of the free base with isopropanol/heptane, with a yield of 84% of theory. The thus obtained nefazodone base is dissolved in isopropanol. 12N HCl is added to this solution and the volatiles are removed under vacuum. The resulting mass is crystallised from isopropanol to give nefazodone hydrochloride (yield, 94%). The product is subsequently dissolved in methylene chloride in an attempt to remove the insoluble impurity, 1,1'-trimethylene-bis-[4-(3-chlorophenyl) piperazine]hydrochloride, by filtration. After removal of the solvent, the nefazodone hydrochloride is crystallised again from isopropanol to give a product melting at 181.0–182.00 C. Since the final yield is not clearly stated, it is estimated, in view of the type and number of treatments contemplated, that it is approximately 74% or less.

In view of the above, it is obvious that, for the time being, the purification of nefazodone is very time-consuming and that this has a considerable influence on the production cost thereof, either with regard to the labour involved or with regard to the inevitable reduction of the final yield as a result of each of the said steps. It is also obvious that the preferred treatment for removing, at least in part, the 1,1'-trimethylene-bis-[4-(3-chlorophenyl)piperazine] hydrochloride (to be called hereinafter "bis-chloro base" for brevity) is the one using methylene chloride. Nevertheless, methylene chloride is rather toxic and entails the use of special security measures.

Therefore, the need for a new way to eliminate or, at least, drastically to reduce the impurities of crude nefazodone to below the respective limit of acceptability, in a low number of steps and using solvents representing fewer drawbacks than methylene chloride, is still very current.

SUMMARY OF THE INVENTION

The research conducted by the present inventors has lead to the surprising discovery that when nefazodone is purified through the formation of the crystalline hydrochloride dihydrate thereof, not only the "bis-chloro base" but also other impurities are practically quantitatively eliminated or, in any case, drastically reduced. Typical examples of such impurities are: 1-(3-hydroxypropyl)-4-(3-chlorophenyl)piperazine (which is hereinafter called "hydroxy base" for brevity), a mass 470 isomer of nefazodone, the 4-chloro isomer of nefazodone (which is hereinafter called "para-chloro isomer" for brevity) and 1-(3-chloropropyl)-4-(3-chlorophenyl)piperazine (hereinafter called "chloro base" for brevity).

In the first aspect thereof, the present invention relates therefore to crystalline nefazodone hydrochloride dihydrate.

Typically, the crystalline nefazodone hydrochloride dihydrate according to the present invention comprises less than 0.5% impurities. Preferably, it comprises less than 0.2% and more preferably still, less that 0.1% impurities.

BRIEF DESCRIPTION OF THE DRAWINGS

In the following paragraphs, reference will be made to charts illustrating the present description. In the drawing figures.

DETAILED DESCRIPTION OF THE INVENTION

Figure 1:
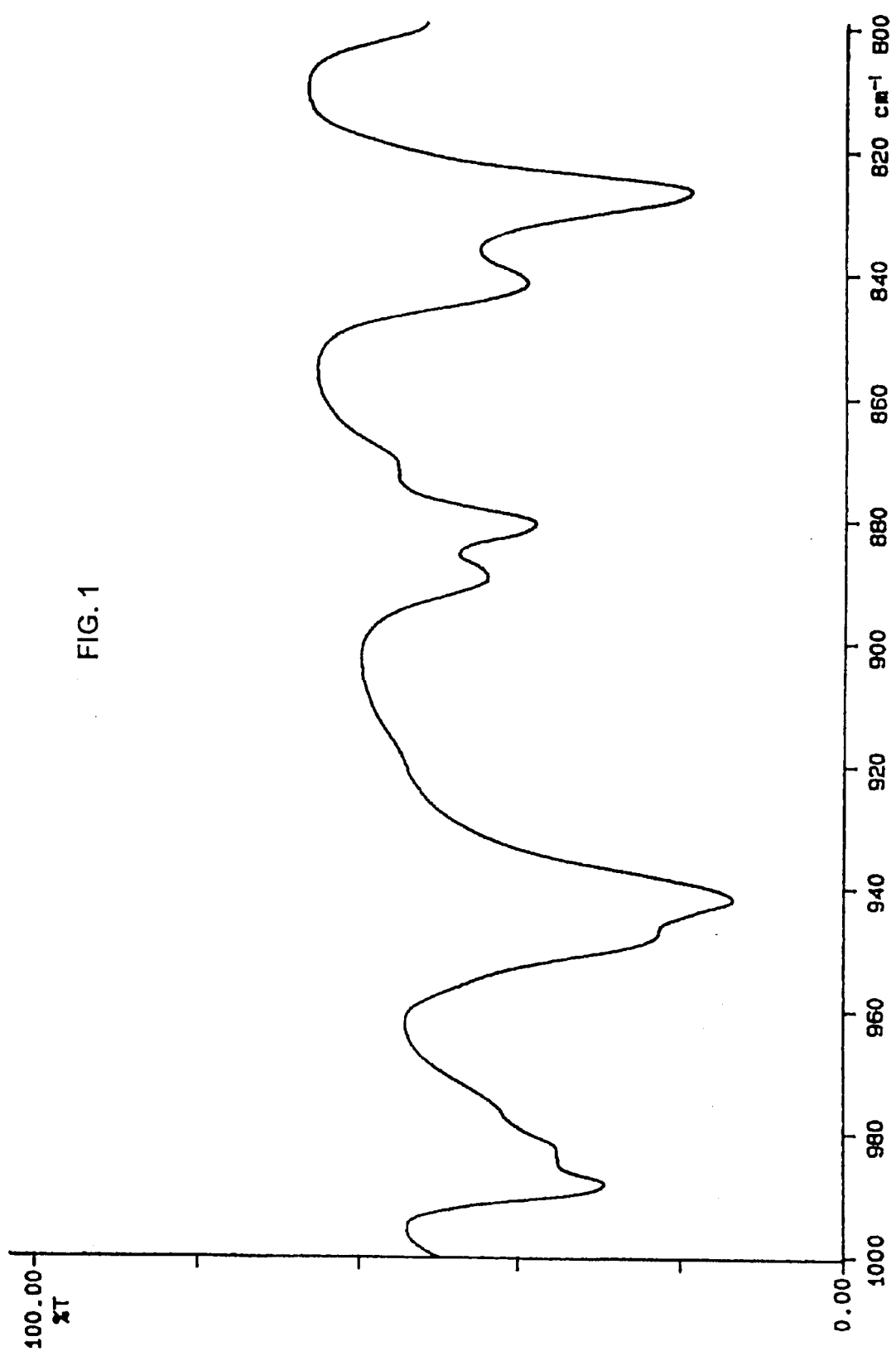
FIG. 1 is the IR spectrum of crystalline nefazodone hydrochloride dihydrate.
Figure 2:
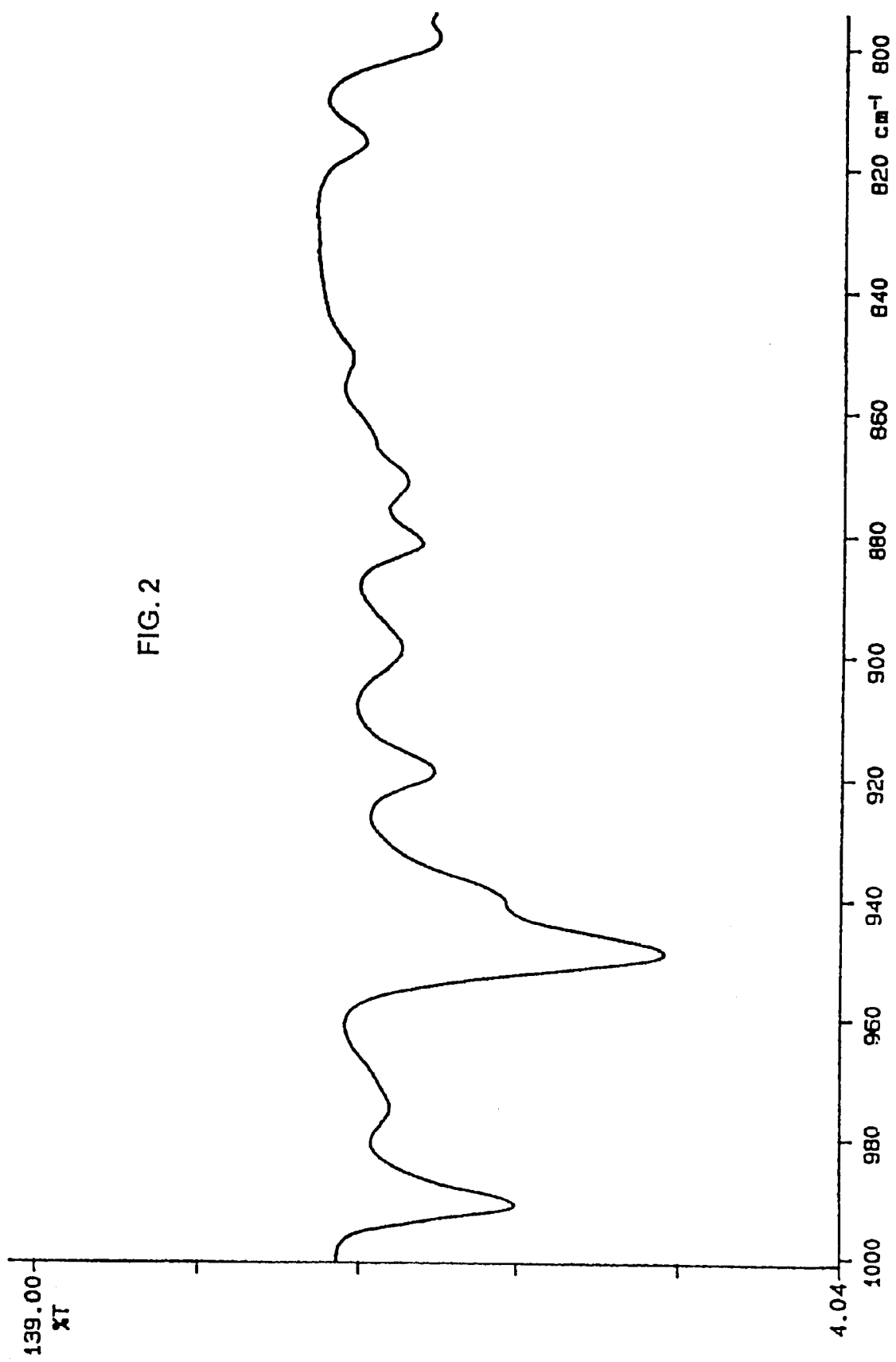
FIG. 2 is the IR spectrum of anhydrous nefazodone hydrochloride, Polymorph A.
Figure 3:
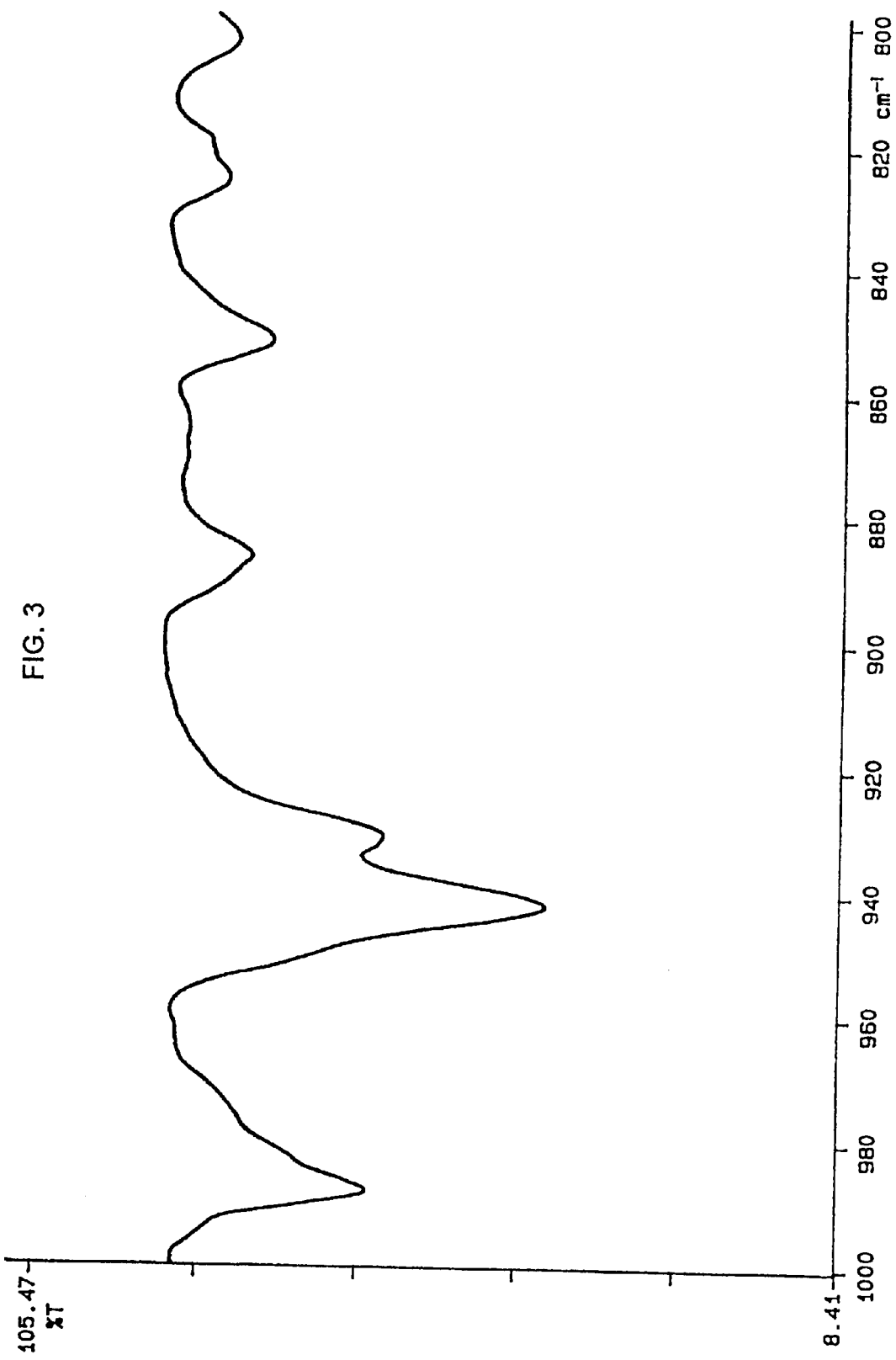
FIG. 3 is the IR spectrum of anhydrous nefazodone hydrochloride, Polymorph B.

The crystalline nefazodone hydrochloride dihydrate of the present invention has an IR spectrum (FIG. 1; Nujol) differing from that of the anhydrous form, Polymorph A (FIG. 2; KBr) and Polymorph B (FIG. 3; KBr), particularly in the region ranging from 800 to 900 cm$^{-1}$.

Figure 4:
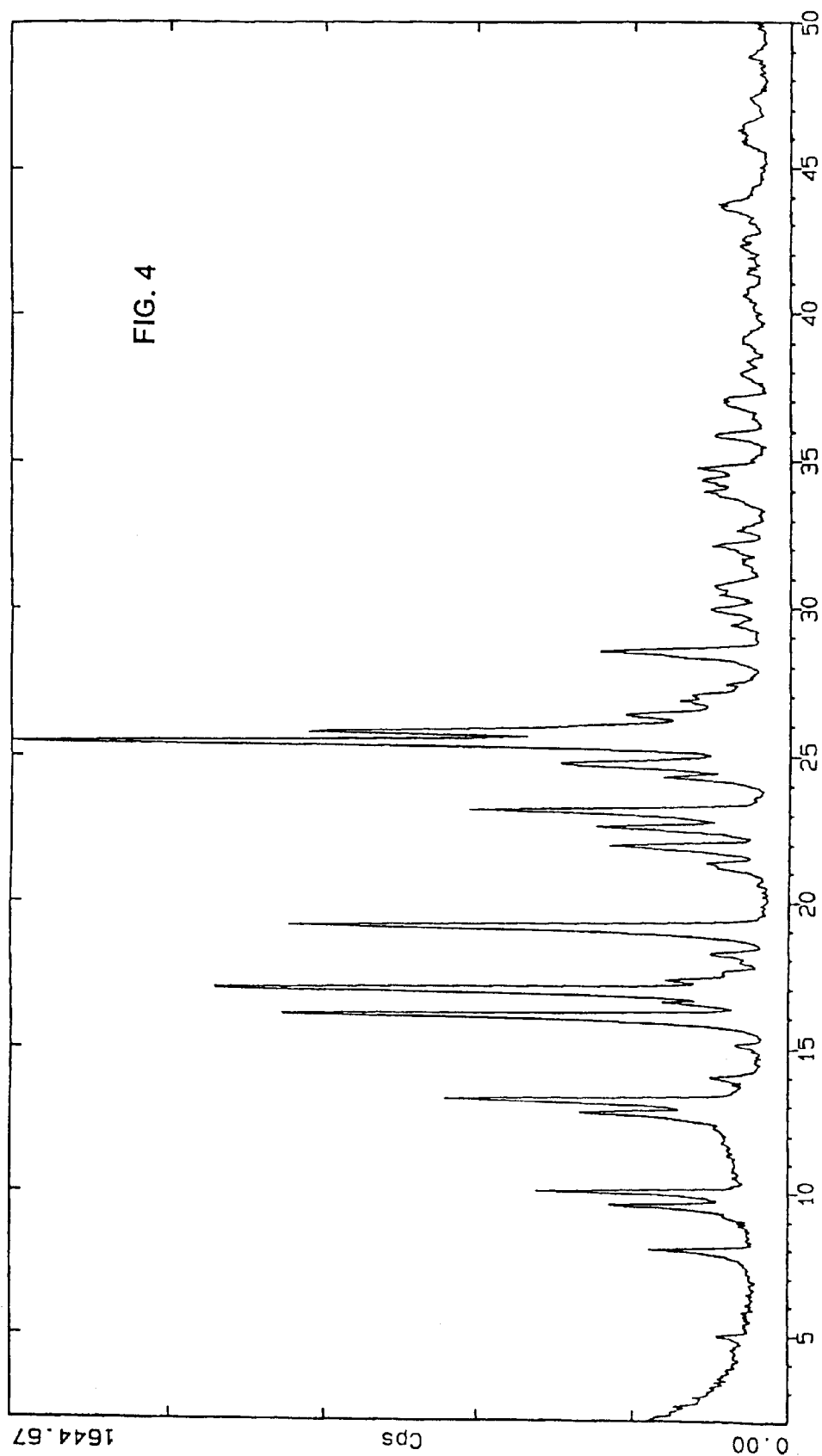
FIG. 4 is the X-ray diffraction spectrum of nefazodone hydrochloride dihydrate.
Figure 5:
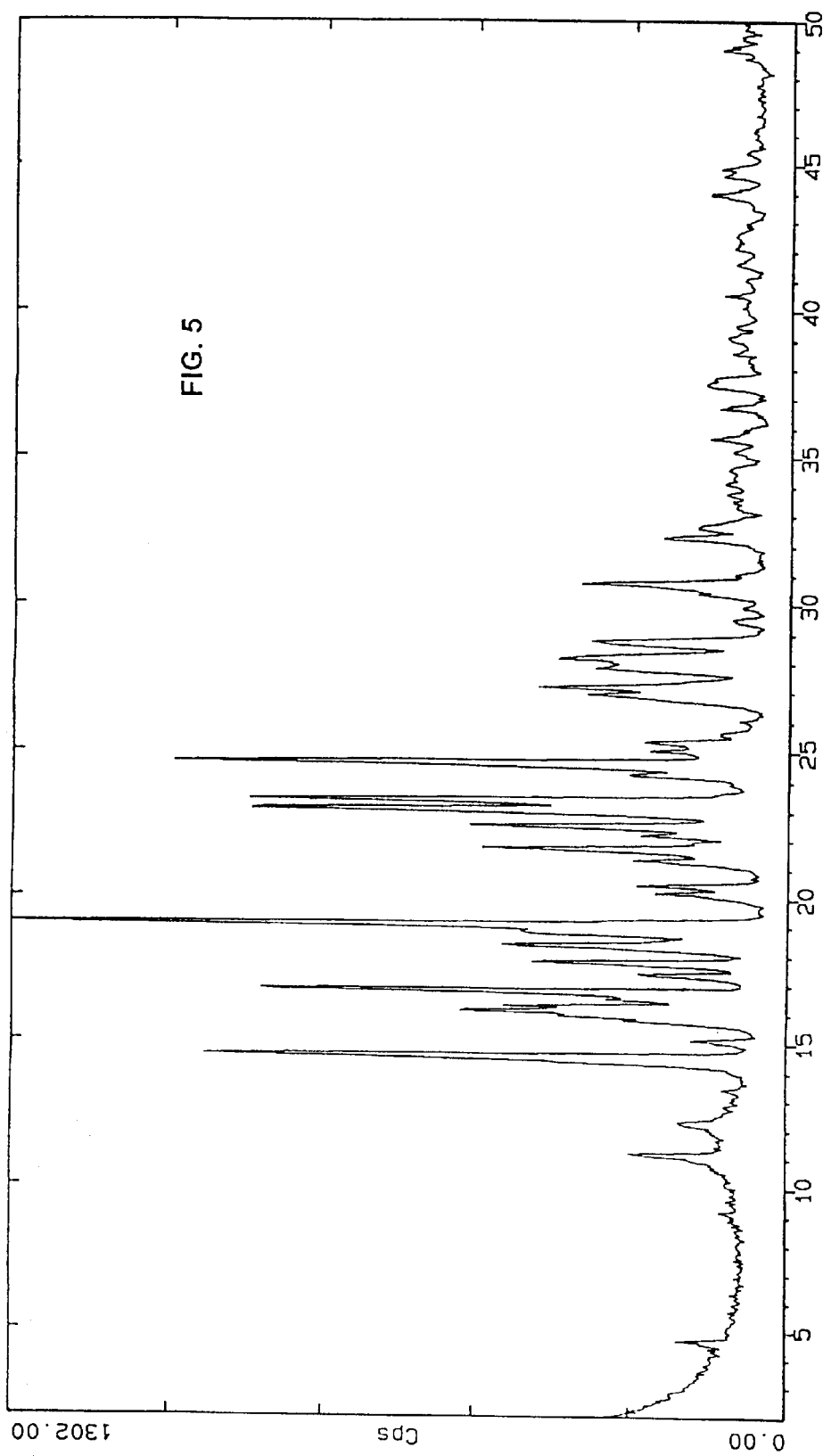
FIG. 5 is the X-ray diffraction spectrum of anhydrous nefazodone hydrochloride, Polymorph A.
Figure 6:
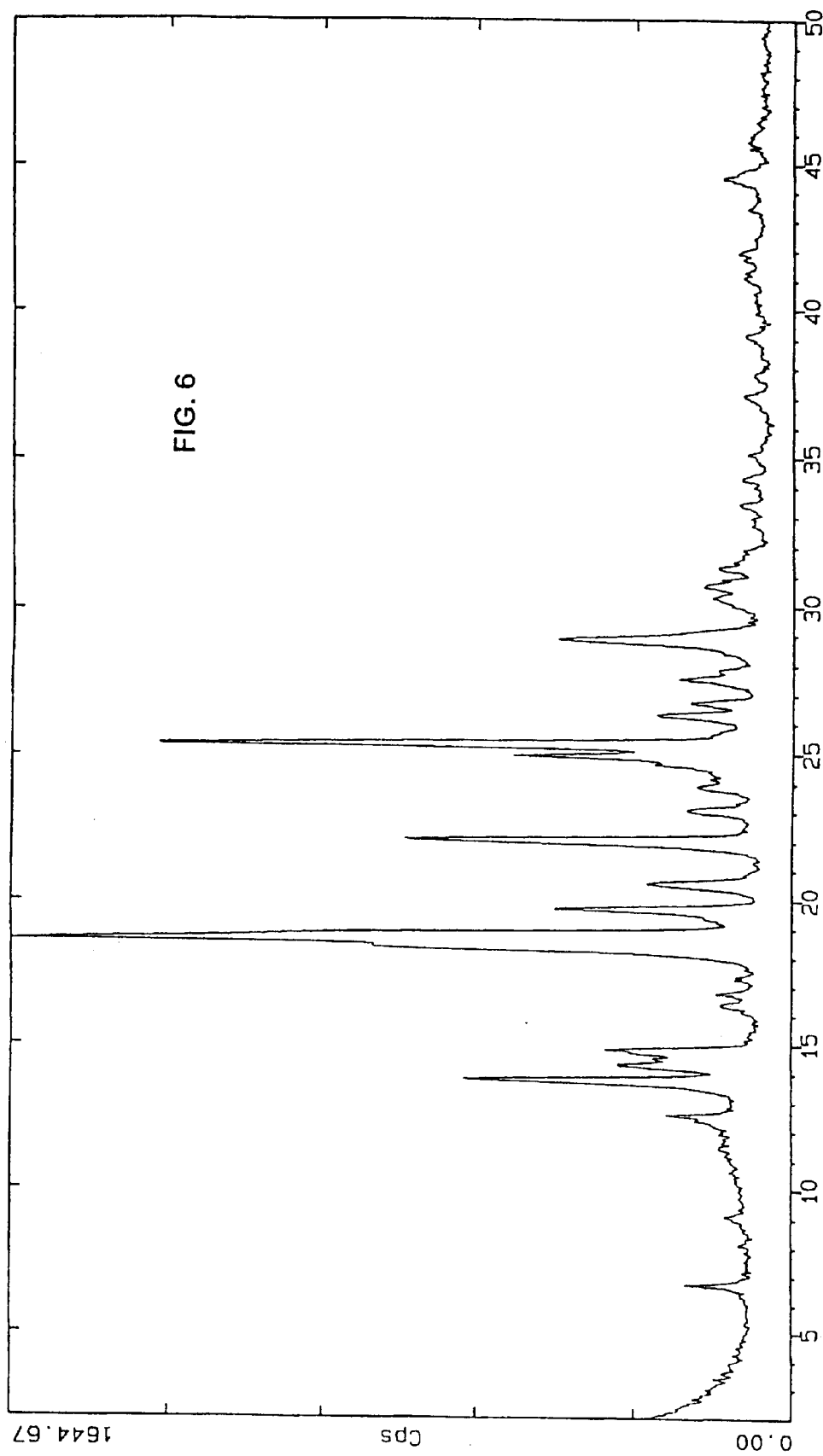
FIG. 6 is the X-ray diffraction spectrum of anhydrous nefazodone hydrochloride, Polymorph B.

It is also different with regard to the X-ray diffraction spectrum (FIGS. 4–6), determined as follows:
  Bragg-Brentano θ/2θ Siemens D-500 geometric diffractometer;
  Cu Kα radiation (λ=1.5418 Å) at 40 kV and 30 mA;
  graphite monochromatic light secondary generator;
  1° divergency window;
  0.050° receiving window;
  2 to 60° 2θ scanning with 0.05° 2θ passage size and 3 seconds measuring time per passage.

It also differs in the thermogravimetric analyses, which were performed with a Mettler TG 50 thermobalance in a 70 μl alumina crucible. The tests were performed with the crucible not provided with lid, or provided with a lid having a centre hole. The lidless tests were performed under an anhydrous nitrogen atmosphere, with the nitrogen (100 ml/min) flowing in the direction of the steam formed.

During the tests performed using the lid with a hole, a "self-atmosphere" may be formed and the displacement of the gas formed is slower.

In the second aspect thereof, the present invention relates to a process for purifying the nefazodone by forming crystalline nefazodone hydrochloride dihydrate in an organic solvent/water mixture comprising at least 0.2 parts by volume of at least one organic solvent for each part by volume of water.

The said mixture preferably comprises at least 1 part (v/v) of organic solvent for each part of water. More preferably still, it comprises at least 2 parts (v/v) of organic solvent for each part of water.

The upper limit of organic solvent contained in the mixture of the present invention varies from solvent to solvent and may reach up to 80 parts by volume for each part of water. It will be preferred in any case to keep it as low as possible, compatibly with the requirements of the process, to reduce the amount of organic solvents used, thereby increasing the productivity of the process and reducing the drawbacks derived from the use of organic solvents.

The organic solvent/water ratio according to the present invention typically ranges from 3:1 to 5:1 (v/v).

The processes of the present invention may be conducted with both water miscible and water immiscible solvents.

Said solvents are preferably chosen from the group formed by low molecular weight aliphatic alcohols, low molecular weight aliphatic chlorides, low molecular weight aliphatic ketones, aliphatic or aromatic hydrocarbons and aprotic dipolar solvents.

Typical examples of preferred organic solvents according to the present invention are $C_1$–$C_5$ aliphatic alcohols, $C_1$–$C_3$ aliphatic chlorides, $C_3$–$C_7$ aliphatic ketones and $C_6$–$C_8$ aliphatic or aromatic hydrocarbons.

Examples of the aliphatic alcohols are ethyl, propyl, isopropyl, butyl, isobutyl, tert-butyl, amyl, isoamyl and tert-amyl alcohols.

Examples of the aliphatic chlorides are methylene chloride, chloroform, carbon tetrachloride, 1,2-dichloroethane, 1,1,2-trichloroethane, 1,1,1-trichloroethane, 1,1,2,2-tetrachloroethylene, 1,2-dichloropropane and 1,3-dichloropropane.

Examples of the aliphatic ketones are acetone, ethylmethylketone, methylpropylketone, isobutylmethylketone, ethylpropylketone, butylmethylketone, diisopropylketone, cyclopentanone and cyclohexanone.

Examples of the hydrocarbons are toluene, xylene, chlorobenzene, cyclohexane and heptane.

An example of an aprotic dipolar solvent is dimethylformamide.

The purification process according to the present invention is carried out using traditional techniques comprising dissolving the crude nefazodone hydrochloride under heating, successive cooling of the solution and removal by filtration of the crystallised product. The most appropriate conditions vary in each case depending on the parameters considered by the man of the art, such as the concentration of the crude product, the type of solvent used and the like. These may be easily determined by the man of the art by way of a few routine tests.

It is also obviously possible to start out from crude nefazodone base, provided that it is first converted to the corresponding hydrochloride.

The crystalline nefazodone hydrochloride dihydrate may also be easily converted, if desired, into anhydrous nefazodone hydrochloride.

A further aspect, therefore, of the present invention is a process for the purification of nefazodone, wherein the crystalline nefazodone hydrochloride dihydrate prepared as described above is crystallised from an anhydrous organic solvent or having a low water content, selected from among those mentioned above, thereby obtaining anhydrous nefazodone hydrochloride.

The present invention is described hereinafter by way of the following examples, which must be deemed to be illustrative and not limitative of the scope of the invention.

EXAMPLE 1

Crystalline Nefazodone Hydrochloride Dihydrate

The crude product was constituted by anhydrous nefazodone hydrochloride (titration=96.37%, HPLC area) containing the impurities listed in Column A of Table 1.

Said crude product (50 g) was suspended in a 5:1 mixture of isoamyl alcohol/water (100 ml; 83 ml of isoamyl alcohol +17 ml of water). In this way, a suspension was obtained which was heated with stirring until the crude product had completely dissolved (65° C., approx.), leaving a clear solution.

It was thereafter seeded, to start the crystallisation, the solution was cooled slowly (approx. 3 h) down to about 0–5° C. and was held at this temperature for about 2 hours.

The crystallised product was removed by filtration and washed over the filter with cold isoamyl alcohol (1×35 ml) and thereafter with cold water (3×50 ml). 58.11 g of a moist white product were obtained. It was thereafter dried in a stove until constant weight, giving 47.36 g of a white product constituted by crystalline nefazodone hydrochloride dihydrate (yield, 88% of theory).

The presence of two molecules of water of crystallisation was determined by the Karl-Fischer method (result: 6.6%).

The HPLC analyses gave the results listed in Column B of Table 1.

TABLE 1

NEFAZODONE HYDROCHLORIDE

| | A<br>Crude<br>% (area) | B<br>Dihydrate<br>% (area) | C<br>Anhydrous<br>% (area) |
|---|---|---|---|
| Nefazodone | 96.37 | 99.93 | 98.32 |
| Hydroxybase | 0.10 | none | 0.06 |
| mass 470 isomer | 2.03 | none | 0.68 |
| p-chloro isomer | 0.10 | 0.03 | 0.08 |
| chloro base | 1.26 | 0.03 | 0.79 |
| bis-chloro base | 0.06 | none | 0.03 |

Comparative Example

Anhydrous Nefazodone Hydrochloride

For comparative purposes, the crude nefazodone hydrochloride (50 g) of the characteristics indicated in Column A of Table 1 was suspended in isoamyl alcohol (450 ml). A suspension was thus obtained, was heated under stirring until complete dissolution of the crude material (approx. 98° C.), leaving a clear solution.

Thereafter, the solution was cooled to about 0–5° C. and was held at this temperature for about 2 hours.

The crystallised product was removed by filtration and washed over the filter with cold isoamyl alcohol (1×25 ml). The moist product weighed 64.23 g. It was dried in a stove until constant weight. In this way, 48.14 g of anhydrous nefazodone hydrochloride were obtained (yield, 96% of theory).

HPLC analysis gave the result indicated in Column C of Table 1.

This test shows that, in the absence of water, it is necessary to use a much greater amount of isoamyl alcohol (5.39 times more) and that it must be heated to a much more elevated temperature. Nevertheless, the purity of the anhydrous nefazodone hydrochloride obtained (Table 1) is clearly inferior to that of the dihydrate according to the present invention.

To verify that the reduction in the amount of organic solvent was a general feature of the present invention, further experiments were performed, the results of which are shown in Table 2.

TABLE 2

| Solvent | Amount of solvent (ml/g) | T (° C.) of solution |
|---|---|---|
| Isoamyl alcohol/Water 5:1 | 2[a] | 65 |
| Isoamyl alcohol | 9 | 98 |
| Isopropyl alcohol/Water 5:1 | 1[b] | 83 |
| Isopropyl alcohol | 22 | 80 |
| Methylene chloride/Water 3:1 | 4[c] | 36 |
| Methylene chloride | 14 | 36 |

[a]equivalent to 1.67 ml of isoamyl alcohol.
[b]equivalent to 0.83 ml of isopropyl alcohol.
[c]equivalent to 3 ml of methylene chloride.

Table 2 shows that, effectively, the present invention entails, together with a greater purity of the end product, a notable reduction in the amount of organic solvent used and this represents an important additional advantage of the present invention over the prior art.

EXAMPLE 2

Anhydrous Nefazodone Hydrochloride from Nefazodone Hydrochloride Dihydrate 40 g of nefazodone hydrochloride dihydrate (6.6% of water of crystallisation, as determined by Karl-Fischer), prepared in a way similar to Example 1, were suspended in 360 ml of isoamyl alcohol. The suspension was heated to dissolution, under stirring (92° C.).

The solution was then allowed to cool. Crystallisation of the product started at 65° C. and this temperature was held for 1 hour. Subsequently, it was slowly cooled to 0–5° C. in about 3 hours and was held at this temperature for approximately 1 hour.

The crystalline product formed was collected by filtration and washed over the filter with cold isoamyl alcohol (1×20 ml). The moist solid weighed 44.86 g. It was dried in a stove until constant weight. In this way, 36.42 g of white crystalline anhydrous nefazodone hydrochloride were obtained (yield, 97% of theory).

Analysis by the Karl-Fischer method of the product dried at 40° C. revealed the presence of 0.01% of water.

The IR analysis revealed that the product obtained was the Polymorph A of nefazodone hydrochloride.

What we claim is:

1. A process for the purification of nefazodone hydrochloride comprising preparing crystalline nefazodone hydrochloride dihydrate by (a) combining crude nefazodone hydrochloride, said crude anhydrous nefazodone hydrochloride selected from the group consisting of crude anhydrous nefazodone hydrochloride, crude nefazodone hydrochloride dihydrate and a crude nefazodone hydrochloride solution, with a mixture of an organic solvent and water which includes at least 0.2 part by volume of at least one organic solvent per part by volume of water; and (b) crystallizing nefazodone hydrochloride dihydrate from said mixture.

2. The process for the purification of nefazodone hydrochloride according to claim 1 wherein said organic solvent is a chlorobenzene.

3. The process for the purification of nefazodone hydrochloride according to claim 1, wherein said mixture contains at least 2 parts (v/v) of said organic solvent per part of water.

4. The process for the purification of nefazodone hydrochloride according to claim 3 wherein said mixture contains at least 3 parts (v/v) of said organic solvent per part of water.

5. The process for the purification of nefazodone hydrochloride according to claim 3 wherein said organic solvent/water mixture is present in a ratio in the range of from 3:1 to 5:1 (v/v).

6. The process for the purification of nefazodone hydrochloride according to claim 3 wherein said organic solvent/water mixture is present in a ratio of 80:1 (v/v).

7. The process for the purification of nefazodone hydrochloride according to claim 1 wherein said organic solvent is selected from the group consisting of low molecular weight aliphatic alcohols, low molecular weight aliphatic chlorides, low molecular weight aliphatic ketones, aliphatic or aromatic hydrocarbons and aprotic dipolar solvents.

8. The process for the purification of nefazodone hydrochloride according to claim 7 wherein said organic solvent is selected from the group consisting of $C_1$–$C_5$ aliphatic alcohols, $C_1$–$C_3$ aliphatic chlorides, $C_3$–$C_7$ aliphatic ketones and $C_6$–$C_8$ aliphatic or aromatic hydrocarbons.

9. The process for the purification of nefazodone hydrochloride according to claim 8 wherein said $C_1$–$C_5$ aliphatic alcohols are selected from the group consisting of ethyl, propyl, isopropyl, butyl, isobutyl, tert-butyl, amyl, isoamyl and tert-amyl alcohols.

10. The process for the purification of nefazodone hydrochloride according to claim 8 wherein said $C_1$–$C_3$ aliphatic chlorides are selected from the group consisting of methylene chloride, chloroform, carbon tetrachloride, 1,2-dichloroethane, 1,1,2-trichloroethane, 1,1,1-trichloroethane, 1,1,2,2-tetrachloroethylene, 1,2-dichloropropane and 1,3-dichloropropane.

11. The process for the purification of nefazodone hydrochloride according to claim 8 wherein said $C_3$–$C_7$ aliphatic ketones are selected from the group consisting of acetone, ethylmethylketone, methylpropylketone, isobutylmethylketone, ethylpropylketone, butylmethylketone, diisopropylketone, cyclopentanone and cyclohexanone.

12. The process for the purification of nefazodone hydrochloride according to claim 8 wherein said hydrocarbons are selected from the group consisting of toluene, xylene, cyclohexane and heptane.

13. The process for the purification of nefazodone hydrochloride according to claim 7, wherein said aprotic dipolar solvent is dimethylformamide.

14. The process for the purification of nefazodone hydrochloride according to claim 1 wherein said step (a) occurs by dissolving said crude nefazodone hydrochloride under heating and said step (b) occurs by cooling the thus obtained solution and separating said crystallized nefazodone hydrochloride dihydrate by filtration.

15. The process for the purification of nefazodone hydrochloride according to claim 14 wherein said crude nefazodone hydrochloride is obtained from a nefazodone base.

16. The process for the purification of nefazodone hydrochloride according to claim 1 wherein said crystalline nefazodone hydrochloride product of step (b) is dissolved in an organic solvent, said organic solvent selected from the group consisting of low molecular weight aliphatic alcohols, low molecular weight aliphatic chlorides, low molecular weight aliphatic ketones, aliphatic or aromatic hydrocarbons and aprotic dipolar solvents, wherein anhydrous nefazodone hydrochloride is obtained by crystallization.

17. Crystalline nefazodone hydrochloride dihydrate, having the chemical Name of 2-[3-[4-(3-chlorophenyl)-1 piperazinyl]-5-ethyl-2,4-dihydro-4-(2-phenoxyethl)-3H-1, 2,4triazol-3-one hydrochloride dihydrate, of formula

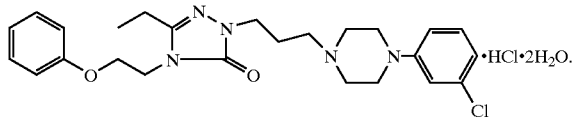

Figure 7:
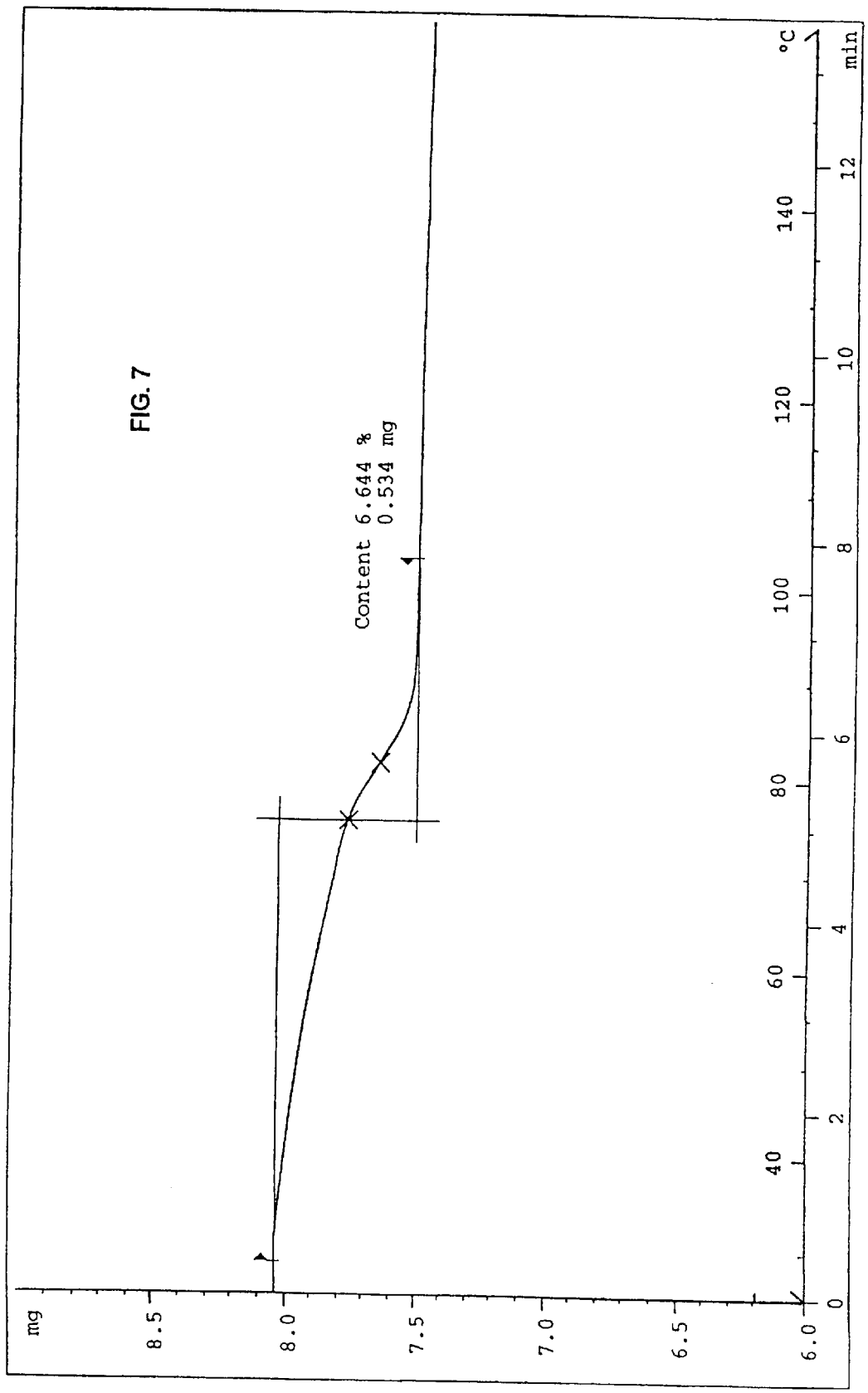
FIG. 7 shows the result of the thermogravimetric analysis of nefazodone hydrochloride dihydrate carried out in a Mettler TG-50 thermobalance in a 70 $\mu$l alumina crucible provided with lid, where the water content is seen to be 6.6%.
Figure 8:
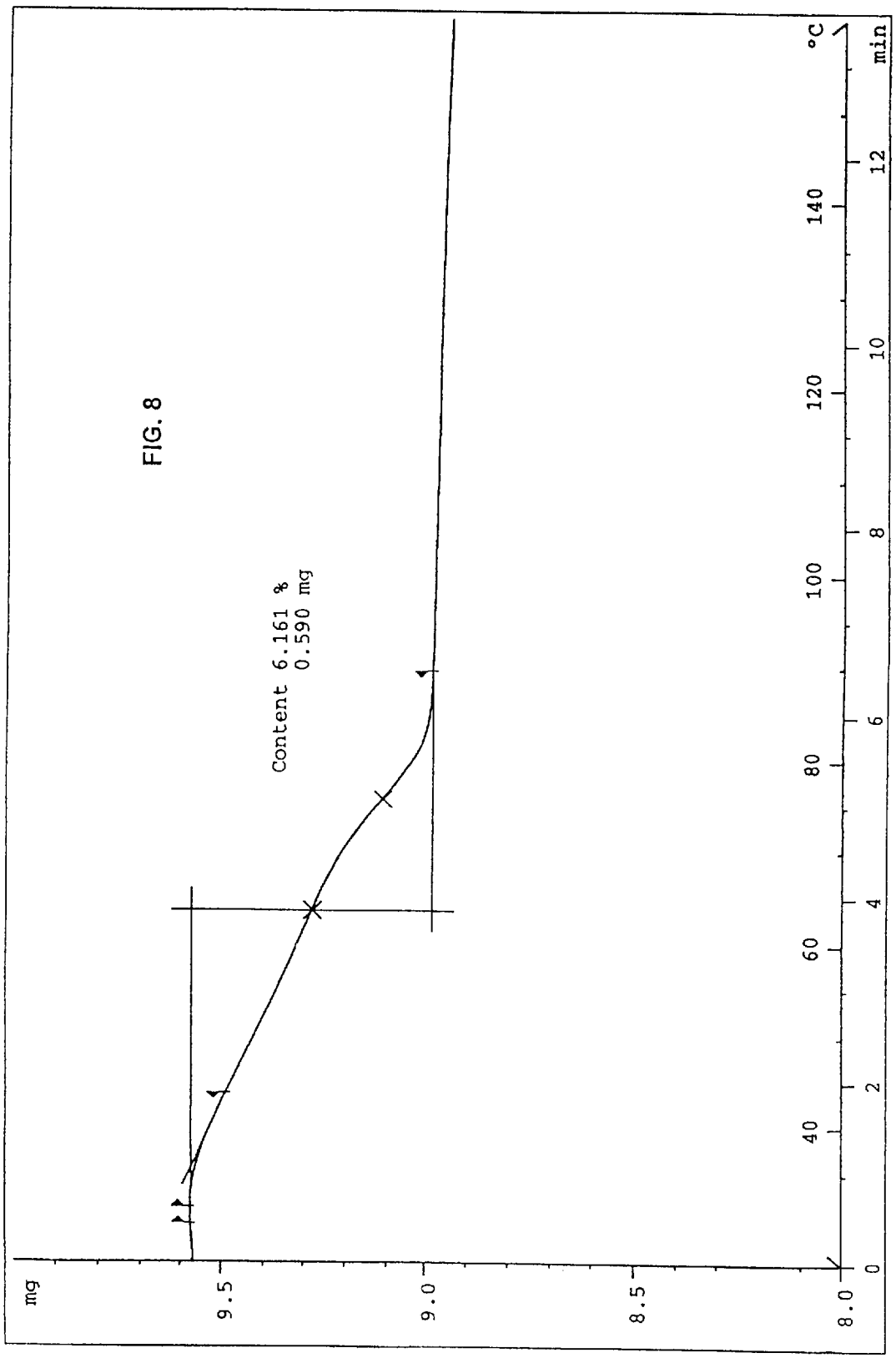
FIG. 8 shows the result of the thermogravimetric analysis of nefazodone hydrochloride dihydrate carried out in a Mettler TG-50 thermobalance in a 70 $\mu$l alumina crucible not provided with lid, where the water content is seen to be 6.2%

18. Crystalline nefazodone hydrochloride dihydrate having the IR spectrum of FIG. 1 and having thermogravimetric analysis of FIGS. 7 and 8.

19. Crystalline nefazodone hydrochloride dihydrate having the X-ray diffraction spectrum of FIG. 4 and having the thermogravimetric analysis of FIGS. 7 and 8.

20. Crystalline nefazodone hydrochloride dihydrate according to at least one of claim 17 to 19, containing less than 0.5% impurities.

21. Crystalline nefazodone hydrochloride dihydrate according to claim 20, containing less than 0.2% impurities.

22. Crystalline nefazodone hydrochloride dihydrate according to claim 21, containing less than 0.1% impurities.

23. The process for the purification of nefazodone hydrochloride wherein said crystalline nefazodone hydrochloride dihydrate according to any one of claims 17, 20, 21, or 22 is dissolved in an organic solvent, said organic solvent selected from the group consisting of low molecular weight aliphatic alcohols, low molecular weight aliphatic chlorides, low molecular weight aliphatic ketones, aliphatic or aromatic hydrocarbons and aprotic dipolar solvents, and crystallizing anhydrous nefazodone hydrochloride therefrom.

24. The process for the purification of nefazodone hydrochloride wherein said crystalline nefazodone hydrochloride dihydrate according to claim 18 is crystallized from an organic solvent, said organic solvent selected from the group consisting of low molecular weight aliphatic alcohols, low molecular weight aliphatic chlorides, low molecular weight aliphatic ketones, aliphatic or aromatic hydrocarbons and aprotic dipolar solvents, to obtain anhydrous nefazodone hydrochloride.

25. The process for the purification of nefazodone hydrochloride wherein said crystalline nefazodone hydrochloride dihydrate according to claim 19 is crystallized from an organic solvent, said organic solvent selected from the group consisting of low molecular weight aliphatic alcohols, low molecular weight aliphatic chlorides, low molecular weight aliphatic ketones, aliphatic or aromatic hydrocarbons and aprotic dipolar solvents, to obtain anhydrous nefazodone hydrochloride.

26. The process for the purification of nefazodone hydrochloride according to claim 23 wherein said organic solvent is anhydrous.

27. The process for the purification of nefazodone hydrochloride according to claim 24 or 25 wherein said organic solvent is anhydrous.

28. The process for the purification of nefazodone hydrochloride according to claim 23 wherein said organic solvent contains less than 7% (v/v) water.

29. The process for the purification of nefazodone hydrochloride according to claim 24 or 25 wherein said organic solvent contains less than 7% (v/v) water.

* * * * *